(12) United States Patent
Parmentier

(10) Patent No.: US 10,470,748 B2
(45) Date of Patent: Nov. 12, 2019

(54) ULTRASONIC ENDOVASCULAR CATHETER WITH EXPANDABLE PORTION

(71) Applicant: C. R. Bard, Inc., Tempe, AZ (US)

(72) Inventor: William Parmentier, Gilbert, AZ (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 15/477,545

(22) Filed: Apr. 3, 2017

(65) Prior Publication Data
US 2018/0280005 A1 Oct. 4, 2018

(51) Int. Cl.
| | | |
|---|---|---|
| A61B 17/00 | (2006.01) | |
| A61B 17/22 | (2006.01) | |
| A61B 17/225 | (2006.01) | |
| A61B 17/221 | (2006.01) | |
| A61B 17/3207 | (2006.01) | |

(52) U.S. Cl.
CPC ............. *A61B 17/00* (2013.01); *A61B 17/22* (2013.01); *A61B 17/221* (2013.01); *A61B 17/225* (2013.01); *A61B 17/22004* (2013.01); *A61B 17/22012* (2013.01); *A61B 17/2251* (2013.01); *A61B 17/320725* (2013.01); *A61B 17/320758* (2013.01); *A61B 2017/22011* (2013.01); *A61B 2017/2212* (2013.01); *A61B 2017/22014* (2013.01)

(58) Field of Classification Search
CPC ... A61B 17/00; A61B 17/22; A61B 17/22004; A61B 17/22012; A61B 17/225; A61B 17/2251; A61B 2017/22014
See application file for complete search history.

(56) References Cited

U.S. PATENT DOCUMENTS

| | | |
|---|---|---|
| 5,030,201 A | 7/1991 | Palestrant |
| 5,403,324 A | 4/1995 | Ciervo et al. |
| 5,498,236 A | 3/1996 | Dubrul et al. |
| (Continued) | | |

FOREIGN PATENT DOCUMENTS

| | | |
|---|---|---|
| DE | 10146011 A1 | 4/2003 |
| EP | 0472368 A2 | 2/1992 |
| (Continued) | | |

OTHER PUBLICATIONS

Circulation Catheter-Based Ultrasound Thrombolysis Shake, Rattle, and Reperfuse Paul G. Yock, Peter J. Fitzgerald https://doi.org/10.1161/01.CIR.95.6.1360.
(Continued)

*Primary Examiner* — Jason E Flick
*Assistant Examiner* — John A Doubrava

(57) ABSTRACT

An apparatus for performing an endovascular procedure using ultrasonic energy includes a catheter comprising a wave guide including an expandable portion for delivering the ultrasonic energy from a source for performing the endovascular procedure. The expandable portion may comprise a plurality of wires formed of a shape memory material. A retractable sheath may be provided for receiving the plurality of wires in the non-deployed position and for being withdrawn to expose the wires in the deployed position. A linear actuator for moving the plurality of wires in a longitudinal direction or a rotary actuator for rotating the plurality of wires may also be provided.

17 Claims, 6 Drawing Sheets

(56) References Cited

U.S. PATENT DOCUMENTS

| | | |
|---|---|---|
| 5,846,218 A | 12/1998 | Brisken et al. |
| 6,022,309 A | 2/2000 | Celliers et al. |
| 6,036,689 A * | 3/2000 | Tu .................. A61B 18/1492 |
| | | 604/103.08 |
| 6,610,077 B1 | 8/2003 | Hancock et al. |
| 6,652,547 B2 | 11/2003 | Rabiner et al. |
| 6,936,025 B1 | 8/2005 | Evans et al. |
| 7,149,587 B2 | 12/2006 | Wardle et al. |
| 7,540,852 B2 | 6/2009 | Nita et al. |
| 7,771,452 B2 | 8/2010 | Pal et al. |
| 7,918,819 B2 | 4/2011 | Karmarkar et al. |
| 8,043,251 B2 | 10/2011 | Nita et al. |
| 8,257,378 B1 | 9/2012 | O'Connor |
| 8,414,543 B2 | 4/2013 | McGuckin, Jr. et al. |
| 8,663,259 B2 | 3/2014 | Levine et al. |
| 9,101,387 B2 | 8/2015 | Plowe et al. |
| 2002/0029054 A1 | 3/2002 | Rabiner et al. |
| 2002/0049409 A1 | 4/2002 | Noda et al. |
| 2002/0077550 A1 | 6/2002 | Rabiner et al. |
| 2003/0176791 A1 | 9/2003 | Rabiner et al. |
| 2004/0164030 A1 | 8/2004 | Lowe et al. |
| 2006/0074441 A1 | 4/2006 | McGuckin et al. |
| 2009/0017293 A1 | 1/2009 | Arai et al. |
| 2013/0060169 A1 | 3/2013 | Yamada et al. |
| 2014/0039491 A1 * | 2/2014 | Bakos ................ A61B 18/1492 |
| | | 606/41 |
| 2014/0236118 A1 | 8/2014 | Unser et al. |
| 2015/0105715 A1 * | 4/2015 | Pikus .................... A61N 7/022 |
| | | 604/22 |
| 2015/0133918 A1 | 5/2015 | Sachar |
| 2015/0157443 A1 | 6/2015 | Hauser et al. |
| 2015/0297258 A1 | 10/2015 | Escudero et al. |
| 2015/0343191 A1 * | 12/2015 | Spano .............. A61B 17/22012 |
| | | 604/22 |
| 2016/0135835 A1 * | 5/2016 | Onuma .............. A61B 17/1604 |
| | | 606/169 |

FOREIGN PATENT DOCUMENTS

| | | |
|---|---|---|
| WO | WO2005112770 A1 | 12/2005 |
| WO | WO2014105754 A1 | 7/2014 |
| WO | WO2014106847 A1 | 7/2014 |

OTHER PUBLICATIONS

International Search Report for PCT/US2018/025208 dated Jun. 18, 2018; European Patent Office.

* cited by examiner

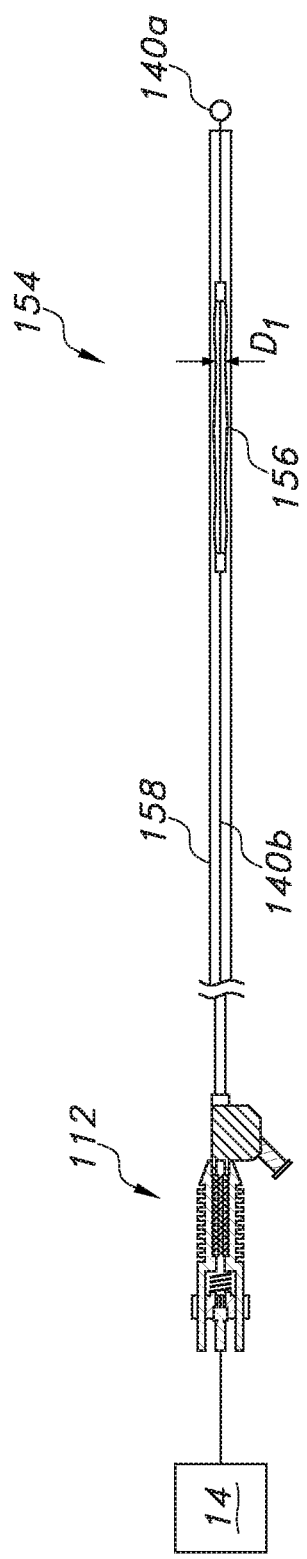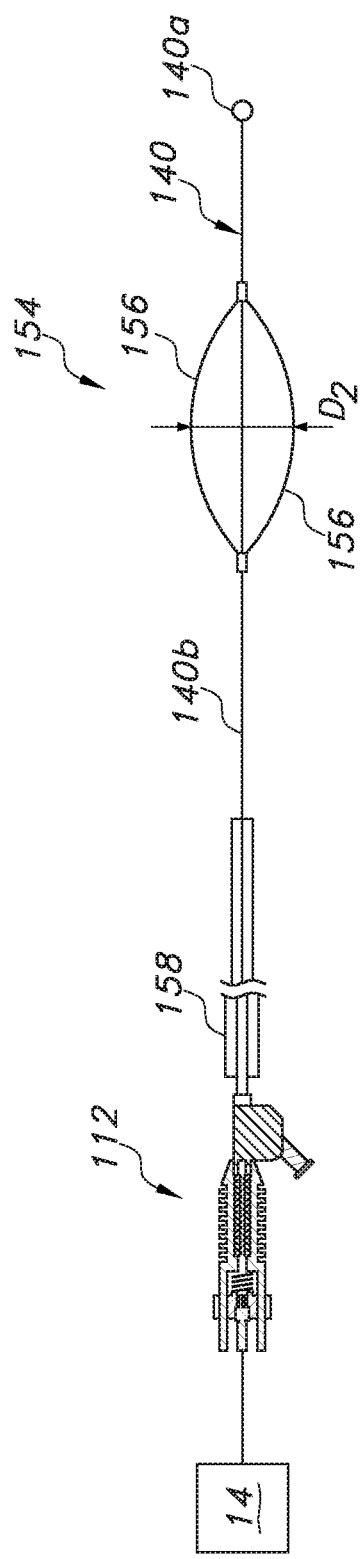
FIG. 6
FIG. 7

ULTRASONIC ENDOVASCULAR CATHETER WITH EXPANDABLE PORTION

TECHNICAL FIELD

This document relates generally to the art of endovascular procedures and, more particularly, to an ultrasonic endovascular catheter for performing a medical procedure, such as an atherectomy or thrombectomy, using an expandable portion.

BACKGROUND

Ultrasonic catheters have been proposed. An example of such a catheter is shown in U.S. Pat. No. 7,540,852, the disclosure of which is fully incorporated herein by reference. While this catheter achieves the desired result of providing enhanced disruption of blood vessel obstructions, the present disclosure proposes certain modifications or improvements to enhance the results achieved during an endovascular procedure in terms of clearing an obstruction from a vessel (such as, for example, an atherectomy for removing atherosclerosis from a blood vessel, or for crossing an occlusion).

SUMMARY

According to a first aspect of the disclosure, an apparatus is provided for performing an endovascular procedure. The apparatus comprises an ultrasonic transducer and a catheter comprising a wave guide for delivering the ultrasonic energy from the transducer for performing the endovascular procedure. The wave guide includes an expandable portion, which may be self-expanding as noted herein, and thus enhances the transmission of energy for clearing a blockage or obstruction.

In one embodiment, the expandable portion includes a first, smaller diameter in a retracted state and a second, larger diameter in a deployed state. The expandable portion may comprise one or more self-expanding wires extending at least partially along an external surface of the wave guide, and may comprise a shape memory material. The one or more wires may include a proximal portion attached to the wave guide, a distal portion attached to the wave guide, and an intermediate portion detached from the wave guide. In some embodiments, the wave guide includes a tip, and the expandable portion is spaced proximally from the tip. The catheter may further include a retractable sheath for receiving the expandable portion in a retracted state. An actuator may also be provided for actuating the wave guide.

According to a further aspect of the disclosure, an apparatus for performing an endovascular procedure using a source of ultrasonic energy is provided. The apparatus includes a catheter including a waveguide for transmitting the ultrasonic energy from the source. The wave guide may include a core having a tip and an expandable portion supported by the core and positioned proximally of the tip.

In one embodiment, the expandable portion comprises one or more self-expanding wires, each including a proximal portion attached to the core, a distal portion attached to the core, and an intermediate portion detached from the core. The one or more wires may comprise a shape memory material. The catheter may further include a retractable sheath for receiving the expandable portion in a retracted state, as well as an actuator for actuating the wave guide.

Still a further aspect of the disclosure pertains to an apparatus for performing an endovascular procedure. The apparatus comprises a catheter that does not carry a balloon, and a wave guide including a core and a plurality of wires fixedly mounted to the core. The wires are expandable from a non-deployed position at least partially closer to the core to a deployed position at least partially spaced from the core.

In some embodiments, an actuator for actuating the plurality of wires is provided. The actuator may comprise: (1) an ultrasonic transducer for exciting or vibrating the plurality of wires; (2) a linear actuator for moving the plurality of wires in a longitudinal direction; and (3) a rotary actuator for rotating the plurality of wires. The catheter may further include a retractable sheath for receiving the plurality of wires in the non-deployed position and being withdrawn to expose the wires in the deployed position. The wave guide may include a tip, and the plurality of wires are spaced proximally of the tip.

BRIEF DESCRIPTION OF THE DRAWING FIGURES

The accompanying drawing figures incorporated herein and forming a part of the specification, illustrate several aspects of the endovascular catheter with an expandable portion and, together with the description, serve to explain certain principles thereof. In the drawing figures:

FIG. 6 is a side view of the catheter with the expandable portion retracted within the sheath;

FIG. 7 is a side view of the catheter with the expandable portion deployed;

Reference will now be made in detail to the presently disclosed embodiments of the inventive aspects of the ultrasonic endovascular catheter with an expandable portion, examples of which are illustrated in the accompanying drawing figures.

DETAILED DESCRIPTION

Ultrasound or ultrasonic catheters provide for disruption of occlusions in blood vessels, such as, for example, plaques, clots, lesions, or like objects that hinder blood flow. Catheters generally include a catheter body (shaft), an ultrasonic energy transmission member disposed within the catheter body and a distal head coupled with the energy transmission member and disposed at or near the distal end of the catheter body. The ultrasonic wave guide transmits ultrasonic energy from an actuator, such as an ultrasonic transducer, to the distal end of the catheter, causing it to vibrate and, thus, disrupt, dissolve, or debulk vascular occlusions (which procedures are generally called atherectomies or thrombectomies). A number of improved features of such an ultrasonic catheter are outlined more fully in the following description.

Figure 1:
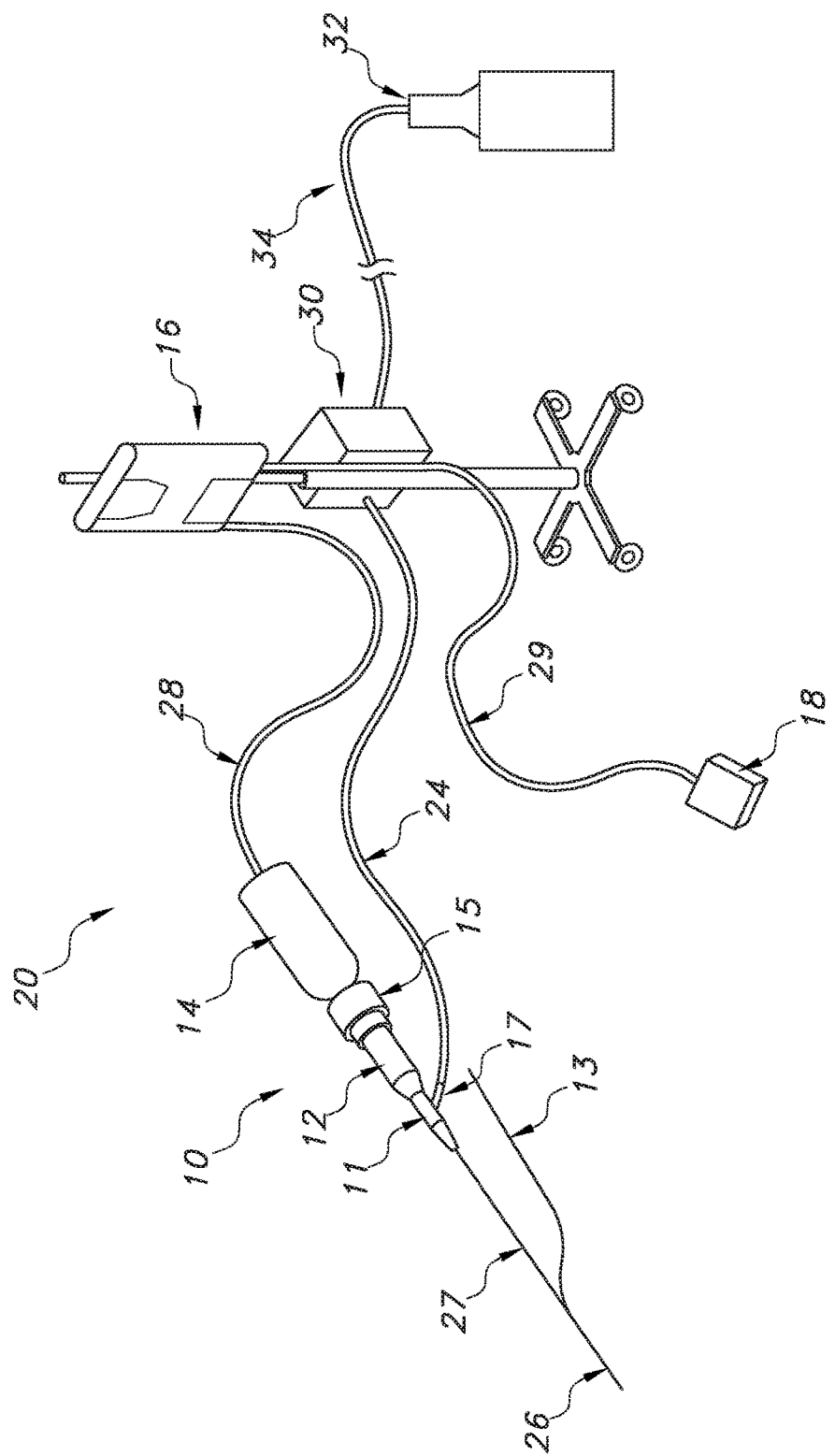
FIG. 1 is a schematic view of a prior art catheter system.

Referring now to FIG. 1, one embodiment of an ultrasonic catheter system 20 includes an ultrasound or ultrasonic catheter 10 and an energy source 16 (which may comprise an ultrasonic generator). Catheter 10 includes a distal end 26 for disrupting occlusions, a catheter shaft or body 27, and a proximal connector 12 for coupling catheter 10 with an ultrasonic transducer 14. Ultrasonic transducer 14 is coupled with source 16 via a connector 28, and generator is coupled with a control, such as a foot-actuated on/off switch 18 via another connector 29. Source 16 provides energy to transducer 14 and, thus, to ultrasonic catheter 10.

Catheter 10 further includes an ultrasonic wave guide (or "core wire"—not shown in FIG. 1) that extends through the catheter body 27 and transmits energy from the transducer 14 to the distal end 26. Some embodiments of catheter 10 include a guidewire, which in FIG. 1 is shown as a so-called "rapid exchange" guidewire 13 and guidewire port, while other embodiments include a proximal guidewire port for over the wire guidewire delivery. In some embodiments, transducer 14 further includes a coupler 15 for coupling the catheter 10 to transducer 14. Connectors 28, 29 may comprise an electric cord or cable or any other suitable connecting devices for coupling on/off switch 18, source 16 and transducer 14. In an alternative embodiment, on/off switch 18 is located on source 16.

In addition to proximal connector 12, ultrasonic catheter 10 may include one or more other various components, such as a Y-connector 11 including a fluid inlet port 17 (or aperture) for passage of irrigation fluid. Inlet port 17 may be removably coupled with an irrigation tube 24, which in one embodiment may be coupled with a fluid refrigerator 30. The refrigerator 30 may, in turn, be coupled with a fluid container 32 via a connector tube 34. This arrangement may be used for introducing one or more fluids into catheter 10. Fluid may be used to cool any part of the device, such as the ultrasonic wave guide, thus helping reduce wear and tear on the catheter 10. In some embodiments, fluid inlet port 17 is located farther proximally on proximal connector 12, to allow fluid to be applied within connector 12. In some embodiments, refrigerated fluid is used, while in other embodiments irrigation fluid may be kept at room temperature. In various embodiments, oxygen supersaturated fluid, lubricious fluid, or any other suitable fluid or combination of fluids may be used, and again, such fluids may be refrigerated or kept room temperature. In an alternative embodiment to that shown in FIG. 1, refrigerator 30 and fluid container 32 are combined in one unit.

Generally, catheter 10 may include any suitable number of side-arms or ports for passage of a guidewire, application of suction, infusing and/or withdrawing irrigation fluid, dye and/or the like, or any other suitable ports or connections. Also, ultrasonic catheters 10 per the disclosure may be used with any suitable proximal devices, such as any suitable ultrasonic transducer 14, energy source 16, coupling device(s) and/or the like. Therefore, the exemplary embodiment shown in FIG. 1 and any following descriptions of proximal apparatus or systems for use with ultrasonic catheters 10 should not be interpreted to limit the scope of the appended claims.

Figure 2:
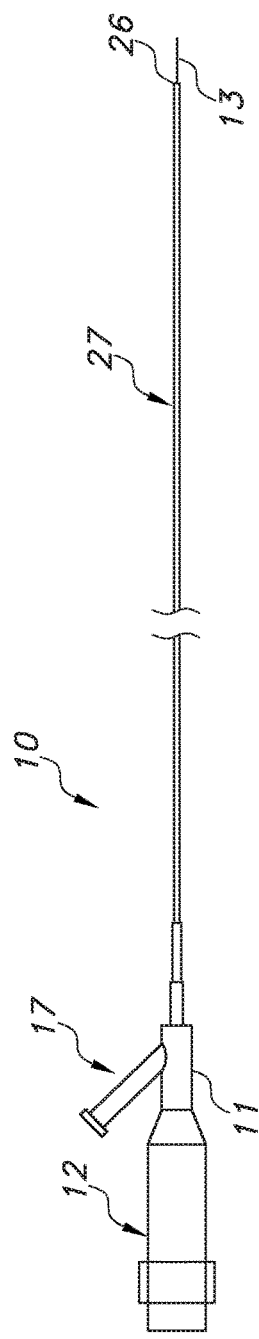
FIG. 2 is a side view illustrating a general layout of a prior art catheter.

Referring now to FIG. 2, an enlarged view of catheter 10 is shown. Proximal connector 12, Y-connector 11, inlet port 17, catheter body 27, distal end 26 and guidewire 13 are all shown. Catheter body 27 is generally a flexible, tubular, elongate member, having any suitable diameter and length for reaching a vascular occlusion for treatment. In one embodiment, for example, catheter body 27 preferably has an outer diameter of between about 0.5 mm and about 5.0 mm. In other embodiments, as in catheters intended for use in relatively small vessels, catheter body 27 may have an outer diameter of between about 0.25 mm and about 2.5 mm. Catheter body 27 may also have any suitable length. As discussed briefly above, for example, some ultrasonic catheters have a length in the range of about 150 cm. However, any other suitable length may be used without departing from the scope of the present disclosure.

Figure 3:
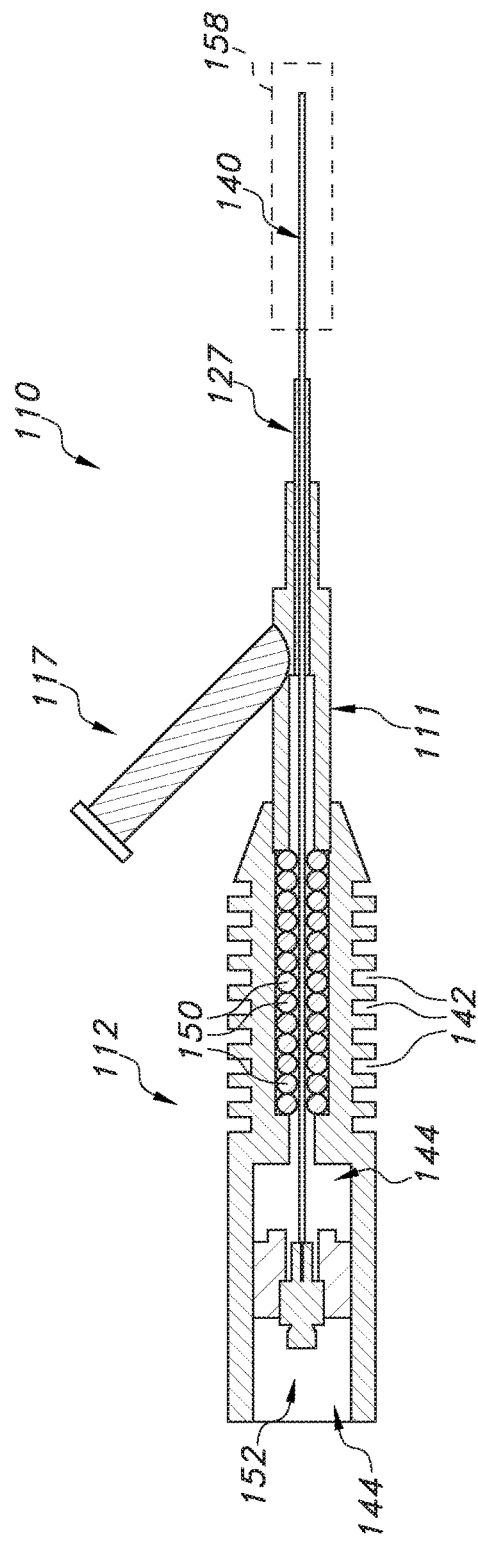
FIG. 3 is a partially cross-sectional, partially cutaway view of a catheter including an ultrasonic wave guide.
Figure 4:
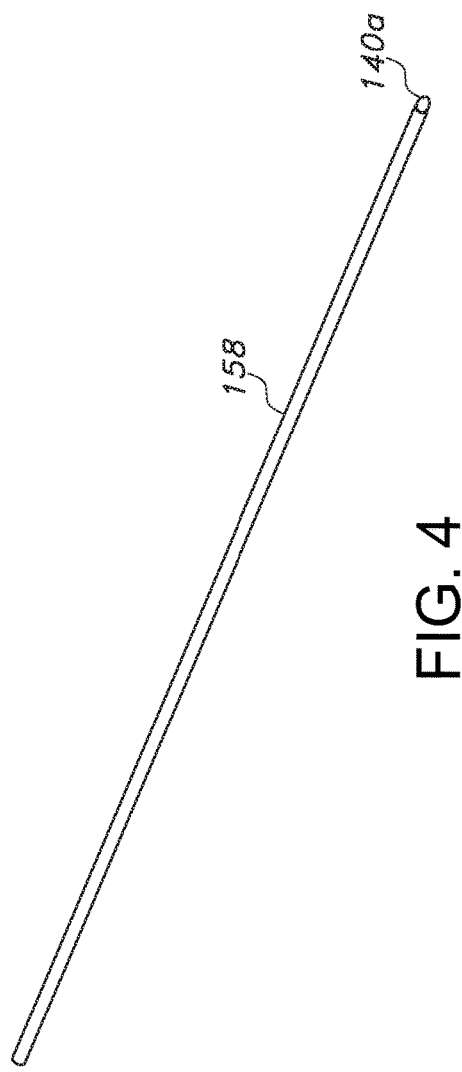
FIG. 4 is a perspective view of a distal end of the catheter with a sheath.
Figure 5:
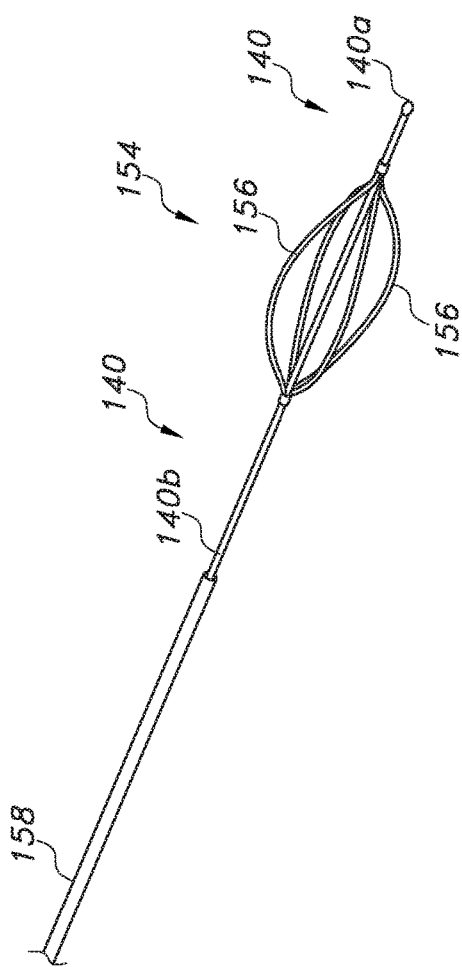
FIG. 5 is a perspective view of the distal end of the catheter with the sheath retracted and the expandable portion deployed.

Referring now to FIG. 3, a proximal portion of one embodiment of an ultrasonic catheter 110 is shown in cross-section, which as can be appreciated does not carry a balloon in the illustrated example. An ultrasonic wave guide 140 extends from a sonic connector 152 distally to a distal end (not shown) of catheter 110. A catheter body 127 of catheter 110 is shown only in part in this figure, whereas catheter body may extend distally to (or near) the distal end of catheter 110, as shown in FIG. 4, with the wave guide 140 also extending a particularly long distance (e.g., 30 centimeters or greater, and typically between about 15 centimeters and 30 centimeters). The catheter body 127 may be a constant diameter, or may have a variable diameter from the proximal to the distal end (such as, for example, wider in diameter at the proximal end near the point of entering the vasculature than at the distal end).

Catheter 110 also includes a proximal housing 112 (or "proximal connector"), having an inner bore 144 (or "inner cavity") in which sonic connector 152, a portion of ultrasonic wave guide 140 and one or more vibration absorbers 150 reside. Housing 112 is coupled with a Y-connector 111, which includes a fluid inlet port 117 (or aperture), and Y-connector 111 is coupled with catheter body 127.

In various embodiments, housing 112 may suitably include one or more surface features 142 for increasing the overall surface area of the outer surface of housing 112. Increased surface area enhances the ability of housing 112 to dissipate heat generated by ultrasonic wave guide 140 out of catheter 110. Surface features 142 may have any suitable size or shape, such as ridges, jags, undulations, grooves or the like, and any suitable number of surface features 142 may be used. Additionally, housing 112 may be made of one or more heat dissipating materials, such as aluminum, stainless steel, any other conductive metal(s), or any suitable non-metallic conductive material(s).

In most embodiments, ultrasonic wave guide 140, such as core wire extends longitudinally through a lumen of catheter body 127 to transmit ultrasonic energy from an ultrasonic transducer 14 (not shown in FIGS. 2 and 3), connected to the proximal end of proximal housing 112, to the distal end of catheter 110. Wave guide 140 may be formed of any material capable of effectively transmitting ultrasonic energy from the ultrasonic transducer 14 to the distal end of catheter body 127, including but not limited to metals such as pure titanium or aluminum, titanium or aluminum alloys, or shape memory materials (such as Nitinol), and may be coated (such as using a polymeric material). The wave guide 140 may be a solid material, or may be woven, braided or formed of helical strands. Again, additional details of ultrasonic wave guides 140 may be found in the documents incorporated by reference. Similarly, reference may be made to the incorporated references for descriptions of housing 112, sonic connector 152, vibration absorbers 150, Y-connector 111 and the like. For example, housing 112 and other features are described in U.S. Pat. No. 7,335,180, the disclosure of which is incorporated herein by reference.

Ultrasonic wave guide 140 typically passes from a sonic connector 152, through bore 144 and Y-connector 111, and then through catheter body 127. Fluid inlet port 117 is in fluid communication with a lumen in Y-connector, which is in fluid communication with a lumen extending through catheter body 127. Thus, fluid introduced into fluid inlet port 117 is typically free to flow into and through catheter body 127 to contact ultrasonic wave guide 140. Fluid may flow out of catheter body 127 through apertures in the distal head (not shown) or through any other suitable apertures or openings, such as apertures located in catheter body 127 itself. Any suitable fluid may be passed through fluid inlet port 117 and catheter body 127, such as refrigerated fluid, lubricious fluid, drug-containing fluid, super-saturated saline or contrast/saline mixture, or the like. Cooling and/or lubricating ultrasonic wave guide 140 may reduce friction and/or wear and tear of ultrasonic wave guide 140, thus prolonging the useful life of ultrasonic catheter 110 and enhancing its performance.

Referring now to FIGS. 4, 5, 6, and 7, it can be understood that the catheter 110 may be provided with an expandable portion 154 at a distal end for aiding in clearing a blockage or obstruction in a vessel. The expandable portion 154 may comprise one or more wires 156, which may be attached directly to the wave guide 140 at the proximal and distal end, such as by swaging, welding, or other secure form of connection. In the illustrated embodiment, four such wires are provided, and thus create an open framework when expanded. The positioning of the expandable portion 154 may be substantially proximal of a tip 140*a* of the wave guide for reasons better understood upon reviewing the following description.

The one or more wires 156 of the expandable portion 154 may comprise a material capable of changing state or shape based on a change in ambient condition, such as temperature. For example, the one or more wires 156 may comprise a shape memory material, such as Nitinol. Thus, in a normal or retracted state, the one or more wires 156 overlie and are located close to or in contact with an external surface of a core 140*b* of the wave guide 140, and when expanded (which may be done selectively by controlling the ambient temperature) are spaced apart from the core 140*b*. Thus, as can be appreciated from FIGS. 6 and 7, this provides the expandable portion 154 with a first, smaller diameter $D_1$ when retracted and a second, larger diameter $D_2$ when deployed. As discussed in more detail below, this increased or expanded diameter may be useful in increasing or enhancing the transmission of energy (such as from the ultrasonic transducer 14) for clearing or debulking a lesion or thrombus. The length and number of the wires 156 may be selected depending on the desired use or outcome (e.g., fewer wires or a shorter length for smaller vessels, and the opposite for larger ones).

In use, and with reference to FIG. 4, the wave guide 140 may be substantially covered by a retractable sheath 158 for purposes of insertion into a vessel with the expandable portion 154 retracted. In the arrangement shown, the tip 140*a* of the wave guide 140 may be exposed from the distal end of the sheath 158, and thus may be used to transmit ultrasonic energy for clearing a blockage in the conventional manner. When the sheath 158 is retracted or withdrawn to expose the distal end of the wave guide 140, the expandable portion 154 may automatically expand as a result of the shape memory material of the one or more wires 156 being exposed and form the deployed or expanded configuration shown (possibly with the addition of a temperature-controlled fluid, such as saline, via the sheath). Ultrasonic energy applied to the wave guide 140 may thus travel not only through the core 140*b*, but also to the one or more wires 156 in a transverse direction. This enhances the ability of the catheter 110 to clear the blockage, potentially reducing the procedure time and avoiding the need for multiple passes.

As noted above, the expandable portion 154 is spaced from the tip 140*a* in a proximal direction. Thus, in one particular manner of use, the tip 140*a* may be initially advanced into a blockage to aid in clearing an initial opening or "pilot" path for the wave guide 140. The expandable portion 154 in the deployed condition may then be used to aid in clearing the remainder of the blockage surrounding the pilot path as the wave guide 140 is advanced. In this manner, the blockage may be substantially cleared in a single pass, and without the need for prolonging the procedure.

Figure 8:
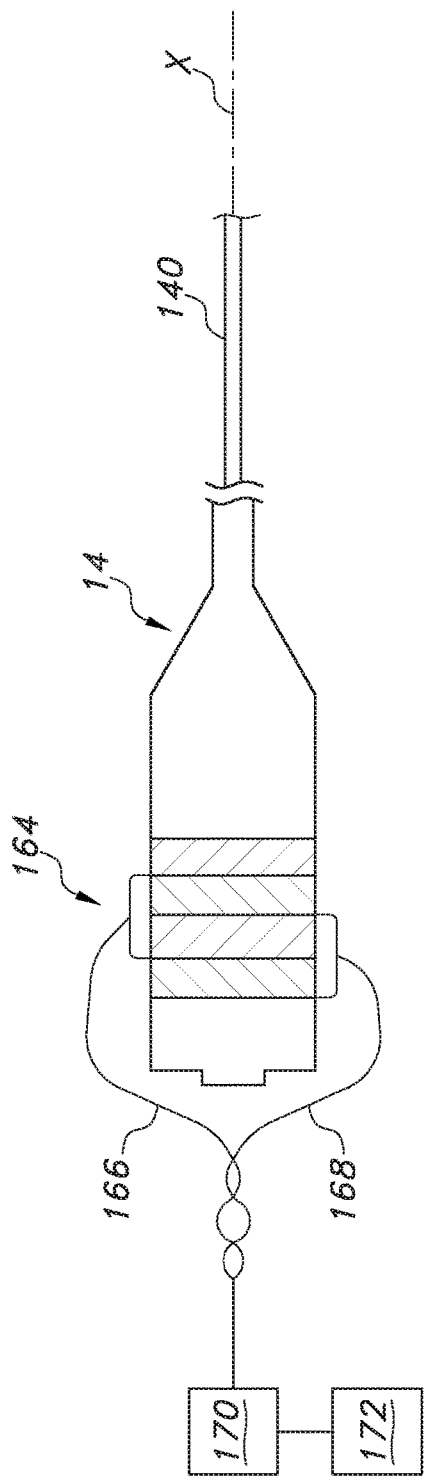
FIG. 8 is a side view of the catheter including a motor.
Figure 9:
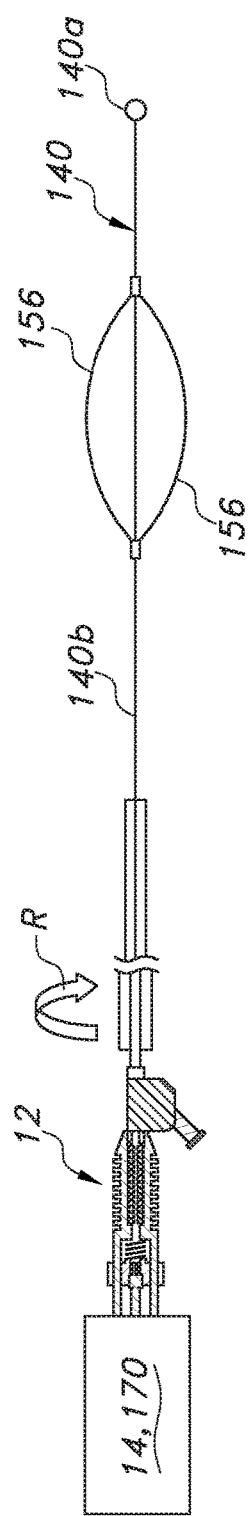
FIG. 9 is a side view illustrating the rotation of the expandable portion by the motor.

Instead of or in addition to the use of ultrasonic energy, the catheter 110 may also be adapted for use in connection with a different type of actuator or source of energy. Referring now to FIGS. 8 and 9, the wave guide 140 or wire may employ an actuator that both vibrates the wave guide through the application of ultrasonic energy, such as from transducer 14, and also causes it to rotate (note arrow R) about its longitudinal axis X, such as through the application for rotational motion to the transducer or any structure connected to the wave guide. In one embodiment, this may be achieved by providing an integral, rotary motor 164 as part of the ultrasonic transducer 14 (which may include the sonic connector 152 therein, or the wave guide 140 may be crimped directly onto the horn of the transducer). Power for the motor 164 may be supplied via a pair of wires 166, 168 (one to ground, one to positive) for causing relative rotation of the wave guide 140, which may be connected to an energy source, such as a power supply 170 for powering both the motor 164 and the transducer 14 (but separate sources could be used, including for example, integral batteries to avoid the need for external wires).

As illustrated, the wires 166, 168 if present may be twisted to allow for the relative rotation without creating binding problems. The rotation of the wave guide 140 may be continuous in one direction, or may be bi-directional (including a rotation of less than 360 degrees in each direction, such that the wave guide may be caused to oscillate about the longitudinal axis X). Control of the rotation may be provided by an associated controller 172 for controlling the power supply 170, which may reverse the flow of current to the motor 164 according to a pre-programmed operation or as a result of manual control provided by a clinician to control the relative direction and amount of rotation. Using the controller 172, the rotation may also be selectively turned on and off, while the vibratory energy is on, or the rotation may be provided while the vibratory energy is turned off. Further details of such an arrangement may be found in U.S. patent application Ser. No. 15/388,335, the disclosure of which is incorporated herein by reference.

Figure 10:
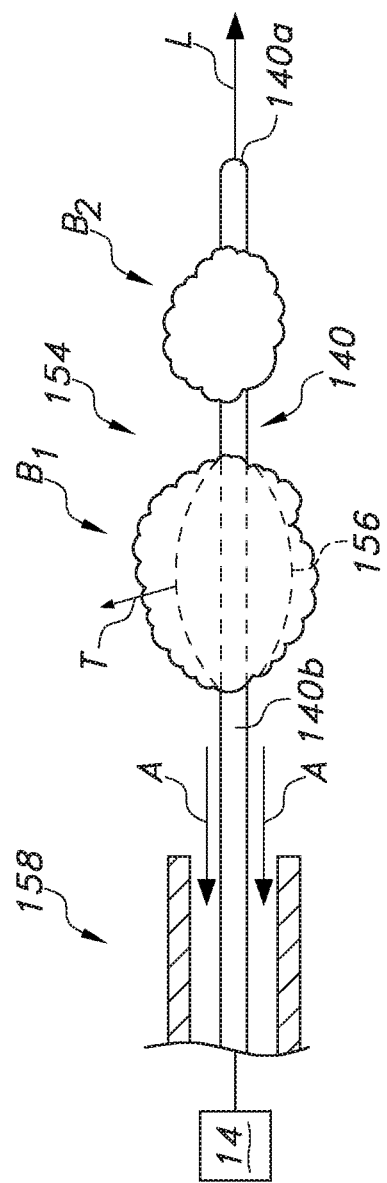
FIG. 10 is a cutaway, partially cross-sectional side view illustrating one method of using the disclosed catheter.

Referring now to FIG. 10, one method of using the catheter is illustrated in connection with a thrombectomy. The wave guide 140 may be ultrasonically excited using transducer 14 and advanced through a first thrombus $B_1$. The sheath 158 may be withdrawn to expose and allow for actuation of the expandable portion 154, which may also be used to destroy the thrombus via the transmission of ultrasonic energy. To remove any dislodged material, aspiration may be achieved using suction applied to the sheath 158, as indicated by action arrows A.

As can be further appreciated, the tip 140*a* in view of its position distal of the expandable portion 154 may also be advanced into and possibly through a second downstream thrombus $B_2$ Thus, the arrangement is capable of clearing multiple blockages in a simultaneous fashion. It can also be appreciated that the tip 140a tends to direct the energy primarily in a longitudinal direction L, whereas the expandable portion 154 directs the energy in a transverse direction T as well.

In summary, an improved catheter 110 includes a self-expanding expandable portion 154 for applying energy for the enhanced treatment of blockages during an endovascular procedure. The expandable portion 154 may comprise one or more wires 156 fabricated of a shape memory material. In connection with a retractable sheath 158, the expandable portion 154 may be selectively deployed or used for transmitting energy for assisting in clearing the blockage, such as from an ultrasonic transducer 14 or other form of actuator (such as motor 164).

The foregoing description has been presented for purposes of illustration. It is not intended to be exhaustive or to limit the embodiments to the precise form disclosed. Obvious modifications and variations are possible in light of the above teachings. All modifications and variations are within the scope of the appended claims when interpreted in accordance with the breadth to which they are fairly, legally and equitably entitled.

What is claimed:

1. An apparatus for performing an endovascular procedure, comprising:
    an ultrasonic transducer for generating ultrasonic energy; and
    a catheter comprising a wave guide having a core and an expandable portion connected to the core, the expandable portion being spaced from the ultrasonic transducer by the core, the core and the expandable portion configured for delivering the ultrasonic energy from the ultrasonic transducer for performing the endovascular procedure;
    wherein the expandable portion comprises one or more self-expanding wires extending at least partially along an external surface of the core of the wave guide, and wherein the one or more self-expanding wires includes a proximal portion attached to the core, a distal portion attached to the core, and an intermediate portion detached from the core.

2. The apparatus of claim 1, wherein the expandable portion includes a first, smaller diameter in a retracted state and a second, larger diameter in a deployed state.

3. The apparatus of claim 1, wherein the expandable portion comprises a shape memory material.

4. The apparatus of claim 1, wherein the wave guide includes a tip, and a distal end of the expandable portion is spaced proximally from the tip.

5. The apparatus of claim 1, wherein the catheter further comprises a retractable sheath for receiving the expandable portion in a retracted state.

6. The apparatus of claim 1, further including an actuator for actuating the wave guide.

7. The apparatus of claim 6, wherein the actuator is selected from the group comprising a linear motor, a rotational motor, and a combination of the two.

8. The apparatus of claim 6, wherein the actuator comprises a linear motor and a rotational motor.

9. An apparatus for performing an endovascular procedure using an ultrasonic transducer, comprising:
    a catheter including a wave guide, the wave guide comprising a core including a tip and an expandable portion supported by the core, a proximal portion of the core being attachable to the ultrasonic transducer, and the expandable portion having a distal end portion attached to the core proximally of the tip, the core and the expandable portion being configured to receive the ultrasonic energy from the ultrasonic transducer, wherein the expandable portion comprises one or more self-expanding wires, each of the one or more self-expanding wires includes: a proximal portion attached to the core, a distal portion attached to the core, and an intermediate portion detached from the core.

10. The apparatus of claim 9, wherein the one or more wires comprise a shape memory material.

11. The apparatus of claim 9, wherein the catheter further comprises a retractable sheath for receiving the expandable portion in a retracted state.

12. The apparatus of claim 9, further including an actuator for actuating the wave guide.

13. The apparatus of claim 12, wherein the actuator is selected from the group comprising a linear motor, a rotational motor, or a combination of the two.

14. An apparatus for performing an endovascular procedure, comprising:
    an ultrasonic transducer;
    a catheter that does not carry a balloon;
    a wave guide including a core and a plurality of wires fixedly mounted to the core, the wires being expandable from a non-deployed position at least partially closer to the core to a deployed position at least partially spaced from the core, the plurality of wires being spaced from the ultrasonic transducer by the core, the ultrasonic transducer vibrating the core and the plurality of wires for performing the endovascular procedure; and
    at least one of: (1) a linear actuator for moving the plurality of wires in a longitudinal direction, or (2) a rotary actuator for rotating the plurality of wires, wherein the wave guide includes a tip, and the plurality of wires have distal ends connected to the core proximally of the tip.

15. The apparatus of claim 14, wherein the catheter further comprises a retractable sheath for receiving the plurality of wires in the non-deployed position and for being withdrawn to expose the wires in the deployed position.

16. The apparatus of claim 14, comprising the rotary actuator for rotating the plurality of wires.

17. The apparatus of claim 14, comprising both a linear motor as the linear actuator and a rotary motor as the rotary actuator.

* * * * *